United States Patent
Drachmann et al.

(10) Patent No.: US 6,427,683 B1
(45) Date of Patent: Aug. 6, 2002

(54) AEROSOL INHALER DEVICE

(76) Inventors: Bo Drachmann, Dalbergstrøget 3; Per Andersen, Snerlehaven 61, both of DK-2630, Taastrup (DK)

( * ) Notice: Subject to any disclaimer, the term of this patent is extended or adjusted under 35 U.S.C. 154(b) by 0 days.

(21) Appl. No.: 09/341,840

(22) PCT Filed: Jan. 16, 1998

(86) PCT No.: PCT/DK98/00021
§ 371 (c)(1),
(2), (4) Date: Jul. 19, 1999

(87) PCT Pub. No.: WO98/31411
PCT Pub. Date: Jul. 23, 1998

(30) Foreign Application Priority Data

Jan. 17, 1997 (DK) .............................................. 0057/97

(51) Int. Cl.⁷ .............................................. A61M 11/00
(52) U.S. Cl. .............................. 128/200.23; 128/200.11
(58) Field of Search ..................... 128/200.11–200.14, 128/200.18, 200.23, 203.21, 203.12; 600/538, 529

(56) References Cited

U.S. PATENT DOCUMENTS

| | | | |
|---|---|---|---|
| 4,592,348 A | * 6/1986 | Waters, IV et al. | 128/200.23 |
| 5,040,527 A | * 8/1991 | Larson et al. | 128/200.23 |
| 5,284,133 A | * 2/1994 | Burns et al. | 128/200.23 |
| 5,297,543 A | * 3/1994 | Larson et al. | 128/200.23 |
| 5,320,094 A | * 6/1994 | Laube et al. | 128/200.23 |
| 5,474,058 A | * 12/1995 | Lix | 128/200.18 |
| 5,724,986 A | * 3/1998 | Jones, Jr. et al. | 128/200.23 |
| 6,062,212 A | * 5/2000 | Davison et al. | 128/200.16 |

FOREIGN PATENT DOCUMENTS

| | | | | |
|---|---|---|---|---|
| GB | 2061116 | * | 5/1981 | 128/200.23 |
| WO | 87/04354 | * | 7/1987 | 128/200.23 |

* cited by examiner

Primary Examiner—John G. Weiss
Assistant Examiner—Teena Mitchell
(74) Attorney, Agent, or Firm—Browdy and Neimark, P.L.L.C.

(57) ABSTRACT

The aerosol inhalation device is manually operated and comprises a holding part (3) for receiving an aerosol container with a valve and an outlet tip, and an inspiratory part (1), which at one end comprises a mouthpiece (2), in which inspiratory part (1) a member (4) for passage of aerosol is provided for receiving the outlet end of the aerosol container and comprising a conduit (5) with an outlet opening for discharging aerosol into the inspiratory part in the direction towards the mouthpiece (2). At the end opposite the mouthpiece (2) the inspiratory part (1) is open towards the surroundings such that air may pass freely from the surroundings past the member (4) for passage of aerosol and out through the mouthpiece (2).

13 Claims, 2 Drawing Sheets

AEROSOL INHALER DEVICE

CROSS REFERENCE TO RELATED APPLICATION

The present application is the national stage under 35 U.S.C. 371 of PCT/EP98/00021, filed Jan. 16, 1998.

BACKGROUND OF THE INVENTION

1. Technical Field of the Invention

The present invention relates to a manually operated aerosol inhalation device comprising a holding part for receiving an aerosol container with a valve and an outlet tip, and an inspiratory part, which at one end comprises a mouthpiece, in which inspiratory part a member for passage of aerosol is provided for receiving the outlet tip of the aerosol container and comprising a conduit with an outlet opening for discharging charging aerosol into the inspiratory part in the direction towards the mouthpiece. Such inhalation devices are for instance known from DK-B-146675, DK-B-164082, DK-B-169464 and DK-B-169863.

2. Prior Art

DK-B-146675 describes an aerosol inhalation device with a swingably openable lid which in its closed position covers an inserted aerosol container to prevent activation thereof and which covers the mouthpiece to prevent it from becoming dirty.

DK-B-164082 describes an aerosol inhalation device with a lid and a rear piece, which are hinged in such a way that the rear piece, when the lid is open, acts as a trigger to facilitate activation of the aerosol container for dispensing a dose of aerosol.

DK-B-169464 describes an aerosol inhalation device, in which the member for passage of aerosol is designed with a special discharge spout which prevents depositing of hygroscopic aerosol particles at the outlet from the member for passage of aerosol.

DK-B-169863 describes another aerosol inhalation device with measures for preventing clogging of hydroscopic aerosol particles at the outlet from the member for passage of aerosol.

Common to these aerosol inhalation devices is, however, that air cannot flow freely through the device past the member for passage of aerosol and out through the mouthpiece, the flow path towards the member for passage of aerosol being partly blocked by the aerosol container. The area of the flow cross section from the surroundings to the member for passage of aerosol to the mouthpiece is thus substantially limited relative to the area of the flow cross section from the member for passage of aerosol to the mouthpiece. This is a problem, as for instance asthmatics, which constitute a big group of users of aerosol inhalation devices, have difficulty in providing sufficient air flow for bringing the active particles of the aerosol down into the lungs. As a matter of fact in case of known devices only approx. ⅓ or less of the active particles is deposited in the lungs, whereas the rest is deposited in the mouth and the throat, where it is undesirable from a medical point of view.

The known manually operated aerosol inhalation devices are used in the manner that the user exhales into free air and then puts the inhalation device to his mouth, inspires and simultaneously presses on the aerosol container, for instance via a trigger, such that a dose of aerosol is dispensed. The air passage next to the container itself is, as mentioned, limited and does not provide the possibility of a proper inhalation through the mouth. The contents of the aerosol are injected as a jet of mist into the mouth towards the rear part of the throat, where the air flow from the nose catches the aerosol and takes its active particles and vehicles down into the lungs. By this method the mouth cavity acts like a relatively dead area with heavy fall-out of particles, and it is only possible for the part of the particles, which remains suspended in the air, to be brought further down into the lungs by means of the air flow from the nasal intake of breath. Through good coordination and technique about one third or less of the active particles is deposited in the lungs by this method, and the rest is deposited at the back of the throat, where it is not desirable from a medical point of view. A comparatively huge intake of breath is required to catch the suspended particles and to take them to the lungs, and in that respect asthmatics are often not able to produce such an intake of breath or account of the asthma. The depositing of the active particles of the aerosol in undesired places may besides have some side effects in the form of local irritations or may for instance result in fungus. Therefore, patients are told to rinse the mouth after use of the aerosol, a request which however, is often not complied with.

In addition to the above manually operated aerosol inhalation devices, breath-activated devices are known, see for instance DK-B-136018, which shows a mechanic device, and WO-A-96/30068, which shows a computer-controlled device. Common to these devices is, however, that they provide a pressure drop, which is used for activating a device for dispensing a dose of the aerosol. These pressure drops, however, undesirable for the above reasons.

U.S. Pat. No. 4,984,158 discloses an apparatus for training a correct breathing performance and coordination with a view to the best possible exploitation of an inhalation device. The apparatus comprises an inspiration member which at one end is provided with a mouthpiece and at its other end is provided with a flow-measuring device which provides a pressure drop, just as in case of the above-mentioned breath activated aerosol inhalation devices. The inspiration member carries a manually operated aerosol container, the discharge tip of which points downwards towards a baffle plate which is to guide the sprayed aerosol towards the mouth of the user. Such a baffle plate is, however, unreliable and thus unsuitable for conducting the aerosol in the desired direction.

Finally, DK-B-151934 discloses a powder inhalation device with a venturi-shaped air passage conduit for spraying a powderous medicament which is taken down into the air passage duct at its narrowest place. There is generally a considerable difference in the considerations forming the basis of the design of an inhalation device for powders, which are allowed to drop down in an inspiratory air flow and the considerations forming the basis of the design of an inhalation device with a pressurized aerosol container, which sprays out the substance.

OBJECT AND SUMMARY OF THE INVENTION

The object of the invention is to provide an aerosol inhalation device which does not suffer from the above drawbacks of the prior art.

The object is according to the invention met by an aerosol inhalation device of the type mentioned by way of introduction and which is characterized in that at the end opposite the mouthpiece the inspiratory part is open towards the surroundings such that air may pass freely from the surroundings past the member for passage of aerosol and out through the mouthpiece, i.e. that the pressure drop at the flow of air from the surroundings to the member for passage of aerosol is not substantially bigger than the pressure drop occuring by the passage of air through the inspiratory part from the member for passage of aerosol to the mouthpiece.

In a preferred embodiment the area of the flow. cross section in the inspiratory part, possibly apart from the area around the member for passage of aerosol, is substantially constant. This contributes to keeping down the pressure drop through the inspiratory part.

In a further preferred embodiment the member for passage of aerosol is at its exterior side aerodynamically designed such that it offers the least possible resistance to the air flow in the inspiratory part and creates the least possible turbulence.

The outlet end of the conduit in the member for passage of aerosol is designed as a diffusor. In this way such a reduction of the velocity of the sprayed out aerosol is obtained that it is mainly taken in by the user through inspiration rather than sprayed into the mouth of the user.

In a practical embodiment the inspiratory part is a cylindrical tube which is open at both ends and between its ends carries the holding part for the aerosol container.

BRIEF DESCRIPTION OF THE DRAWINGS

The invention will now be explained in detail in the following by means of an example of an embodiment with reference to the drawing, in which.

DETAILED DESCRIPTION OF THE PREFERRED EMBODIMENTS OF THE INVENTION

The inhalation device comprises an inspiratory part 1, which in the present example of an embodiment is constituted of a circular cylindrical tube open at both ends. One end of the tube constitutes a mouthpiece 2. Between its ends the inspiratory part 1 carries a holding part 3 for an aerosol container.

The aerosol container which is not shown is of the conventional type with a dispensing valve with an outlet tip in the form of a small tube.

Figure 1:
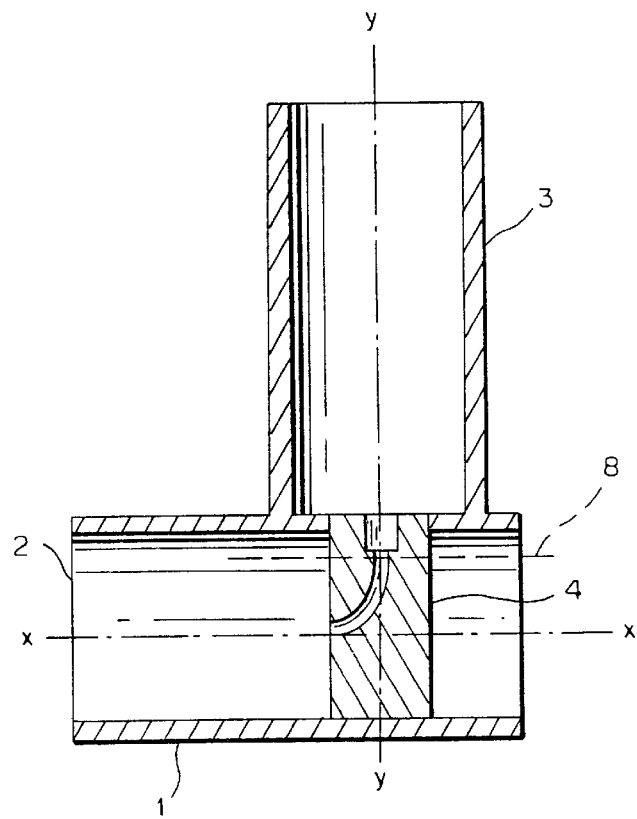
FIG. 1 is a vertical sectional view through an inhalation device according to the invention.
Figure 2:
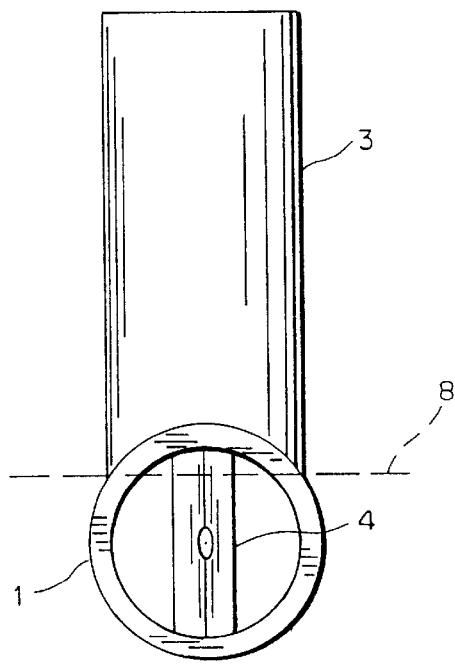
FIG. 2 is a view of the inhalation device seen in the direction of the arrow II in FIG. 1.
Figure 3:
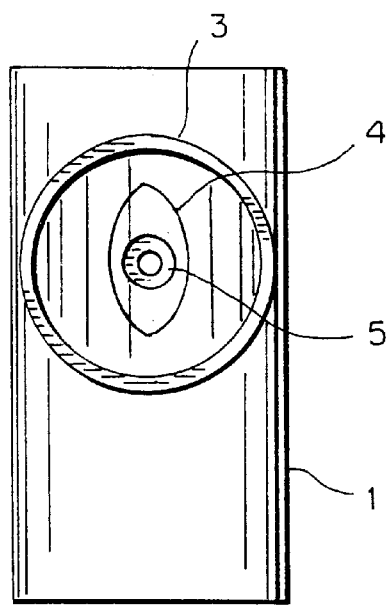
FIG. 3 is a view of the inhalation device, seen from above.
Figure 4:
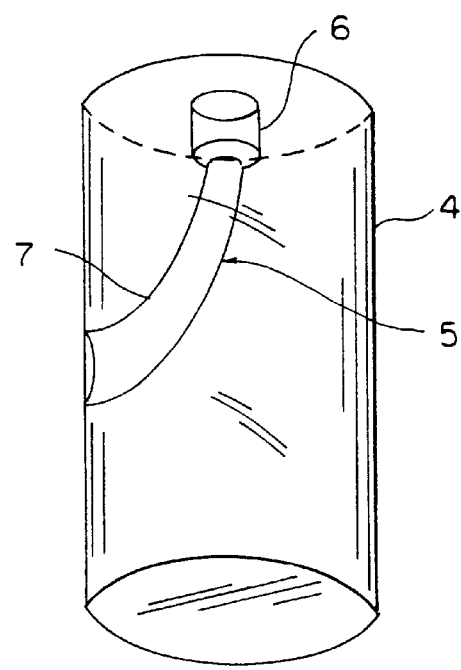
FIG. 4 is a view of the member for passage of aerosol, shown transparently in perspective obliquely from below.

In the inspiratory part 1 a member 4 for passage of aerosol is provided, said member being shown in detail in FIG. 4. The member 4 for passage of aerosol consists in the embodiment shown in a cylindric, aerodynamically designed body extending transversely through the inspiratory part 1 and having the elliptical cross section shown in FIG. 3 in a plane 8 parallel to the central longitudinal axis x—x of inspiratory part 1 and perpendicular to the central axis y—y of the holding part 3. The member 4 for passage of aerosol has a conduit 5 with a first portion 6 adapted to receive the outlet tip of the aerosol container, and a second portion 7 designed as a conical tube for taking aerosol from the outlet tip into the inspiratory part 1 in a direction towards the mouthpiece 2, the velocity of the aerosol being at the same time reduced.

Apart from the conduit 5, no connection between the compartment in the holding part 3 and the inspiratory part 1 has to be provided.

The inhalation device is used in the manner that the user takes the mouthpiece 2 into his mouth, expiration is made through the inspiratory part 1, which is possible because it is open at both ends, and then a pressure is exerted on the aerosol container for release of a dose of aerosol and inhalation is performed without removal of the inhalation device from the mouth. By use of this inhalation device it is to be expected that approx. 60% of the active substance will be deposited in the lungs compared to at the most 30% by use of the known devices, for which reason it will be possible to reduce the size of the dosage. Due to the fact that the inspiration of the user takes the aerosol into the mouth cavity and further down into the lungs, it will moreover be possible to reduce the pressure in the aerosol container relative to what is the case with commonly used devices.

Even though the inspiratory part 1 here is shown and described as being circular cylindrical, it should be understood that other types of cross sections may be used, for instance oval ones. It should further be understood that a certain variation in the cross section area is not excluded. The important thing is that no flow resistance is present through the inspiratory part and that the user may breathe substantially freely through it.

We claim:
1. A manually operated aerosol inhalation device comprising
   a tubular inspiratory part with an internal cross sectional area, having at one end a mouthpiece and having an inlet opening with an opening area in another end opposite the mouthpiece,
   a holding part for receiving an aerosol container with a valve and an outlet tip, and being situated externally on the tubular inspiratory part at a first portion thereof,
   a member for passage of aerosol being provided in said first portion for receiving the outlet tip of the aerosol container and comprising a conduit with an outlet opening for discharging aerosol into the inspiratory part in a direction towards the mouthpiece, said member extending transversely in the tubular inspiratory part and occupying part of the internal cross sectional area in the first portion of the tubular inspiratory part,
   a second portion of the tubular inspiratory part extending from the first portion to the inlet opening and a third portion of the tubular inspiratory part extending from the first portion to the mouthpiece, the first portion being situated intermediate of the second portion and the third portion,
   said third portion having a constant internal cross sectional area equal to said opening area,
   wherein the first portion, second portion and third portion reduce a back pressure or pressure drop in use.
2. An aerosol inhalation device according to claim 1, wherein said member for passage of aerosol is aerodynamically designed to have an elliptical cross section in a plane parallel to a central longitudinal axis of the tubular inspiratory part and perpendicular to a central longitudinal axis of the holding part, said elliptical cross section having a larger dimension in a direction parallel to the central longitudinal axis of the tubular inspiratory part than in a direction perpendicular thereto.
3. An aerosol inhalation device according to claim 1, wherein an outlet end of the conduit in the member for passage of aerosol is designed as a diffusor.
4. An aerosol inhalation device according to claim 1, wherein the inspiratory part is a cylindrical tube, which is open at both ends, and between said ends carries the holding part for the aerosol container.

5. A manually operated aerosol inhalation device comprising
- a tubular inspiratory part with an internal cross sectional area, having at one end a mouthpiece and having an inlet opening with an opening area in another end opposite the mouthpiece,
- a holding part for receiving an aerosol container with a valve and an outlet tip, and being situated externally on the tubular inspiratory part at a first portion thereof,
- a member for passage of aerosol being provided in said first portion for receiving the outlet tip of the aerosol container and comprising a conduit with an outlet opening for discharging aerosol into the inspiratory part in a direction towards the mouthpiece, said member extending transversely in the tubular inspiratory part occupying part of the internal cross sectional area in the first portion of the tubular inspiratory part,
- a second portion of the tubular inspiratory part extending from the first portion to the inlet opening and a third portion of the tubular inspiratory part extending from the first portion to the mouth piece, the first portion being situated intermediate of the second portion and the third portion,
- said member for passage of aerosol being aerodynamically designed to have an elliptical cross section in a plane parallel to a central longitudinal axis of the tubular inspiratory part and perpendicular to a central longitudinal axis of the holding part, said elliptical cross section having a larger dimension in a direction parallel to the central longitudinal axis of the tubular inspiratory part than in a direction perpendicular thereto,
- wherein the first portion, second portion and third portion reduce a back pressure or pressure drop in use.

6. An aerosol inhalation device according to claim 5, wherein the member for passage of aerosol has a cross section shaped as a longitudinal section of an elliptical football.

7. An aerosol inhalation device according to claim 6, wherein an outlet end of the conduit in the member for passage of aerosol is designed as a diffusor.

8. An aerosol inhalation device according to claim 5, wherein the inspiratory part is a cylindrical tube, which is open at both ends, and between said ends carries the holding part for the aerosol container.

9. An aerosol inhalation device according to claim 5, wherein said third portion has a constant internal cross sectional area equal to said opening area.

10. A manually operated aerosol inhalation device comprising:
- a holding part adapted to receive an aerosol container with a valve and an outlet tip;
- a tubular inspiratory part engaged to the holding part and having a first open end comprising a mouthpiece in communication with a second open end;
- a member for passage of aerosol adapted to receive the outlet tip of the aerosol container being engaged to the tubular inspiratory part between the first open end and the second open end and occupying part of a cross sectional area of the tubular inspiratory part, the member having a conduit with an outlet for discharging aerosol into the inspiratory part in a direction towards the first open end,
- wherein said member for passage of aerosol is aerodynamically designed to have an elliptical cross section in a plane parallel to a central longitudinal axis of the tubular inspiratory part and perpendicular to a central longitudinal axis of the holding part, said elliptical cross section having a larger dimension in a direction parallel to the central longitudinal axis of the tubular inspiratory part than in a direction perpendicular thereto, and
- wherein the tubular inspiratory part reduces a back pressure or pressure drop in use.

11. An aerosol inhalation device according to claim 10, wherein the member for passage of aerosol has a cross section shaped as a longitudinal section of an elliptical football.

12. An aerosol inhalation device according to claim 10, wherein an outlet end of the conduit in the member for passage of aerosol is designed as a diffusor.

13. An aerosol inhalation device according to claim 10, wherein the inspiratory part is a cylindrical tube, which is open at both ends, and between said ends carries the holding part for the aerosol container.

* * * * *